(12) United States Patent
Kawamura

(10) Patent No.: US 10,617,378 B2
(45) Date of Patent: Apr. 14, 2020

(54) RADIATION IMAGE PROCESSING DEVICE, METHOD, AND PROGRAM CONFIGURED TO ELIMINATE SCATTERED RADIATION BASED ON A VIRTUAL GRID CHARACTERISTIC

(71) Applicant: FUJIFILM Corporation, Tokyo (JP)

(72) Inventor: Takahiro Kawamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 272 days.

(21) Appl. No.: 15/614,620

(22) Filed: Jun. 6, 2017

(65) Prior Publication Data

US 2017/0360391 A1 Dec. 21, 2017

(30) Foreign Application Priority Data

Jun. 21, 2016 (JP) ................................ 2016-122349

(51) Int. Cl.
*A61B 6/00* (2006.01)
*G01T 1/00* (2006.01)

(52) U.S. Cl.
CPC .......... *A61B 6/5282* (2013.01); *A61B 6/5294* (2013.01); *A61B 6/542* (2013.01);
(Continued)

(58) Field of Classification Search
CPC ....... A61B 6/52; A61B 6/5205; A61B 6/5258; A61B 6/5282; A61B 6/5294; A61B 6/54;
(Continued)

(56) References Cited

U.S. PATENT DOCUMENTS 5,270,925 A * 12/1993 Stegehuis ............ H04N 5/3205
128/922
5,666,391 A * 9/1997 Ohnesorge ........... A61B 6/5282
378/7
(Continued)

FOREIGN PATENT DOCUMENTS

JP H09149895 6/1997
JP 2004101195 4/2004
(Continued)

OTHER PUBLICATIONS

English translation of JPH09-149895 A by EPO Patent Translate on Oct. 10, 2019.*
(Continued)

*Primary Examiner* — Allen C. Ho
(74) *Attorney, Agent, or Firm* — JCIPRNET

(57) ABSTRACT

When performing processing for eliminating scattered radiation included in radiation transmitted through a subject on a radiation image captured by irradiating the subject with radiation, an imaging condition acquisition unit acquires imaging conditions, and a distance information acquisition unit acquires distance information representing the distance between the subject and a radiation detector. A scattered radiation information acquisition unit acquires scattered radiation component information representing a scattered radiation component of radiation included in the radiation image based on at least the imaging conditions, and a correction unit corrects the scattered radiation component information based on the distance information. A scattered radiation elimination unit performs scattered radiation elimination processing of the radiation image based on the corrected scattered radiation component information.

8 Claims, 10 Drawing Sheets

(52) U.S. Cl.
CPC ............ *A61B 6/4291* (2013.01); *A61B 6/588* (2013.01); *A61B 6/589* (2013.01); *G01T 1/00* (2013.01)

(58) Field of Classification Search
CPC .......... A61B 6/542; A61B 6/58; A61B 6/582; A61B 6/585; A61B 6/588; A61B 6/589; A61B 6/42; A61B 6/4208; A61B 6/4233; A61B 6/4241; A61B 6/4291
USPC ................................................ 378/7, 62, 207
See application file for complete search history.

(56) References Cited

U.S. PATENT DOCUMENTS

| | | | |
|---|---|---|---|
| 5,960,058 A | 9/1999 | Baba et al. | |
| 6,385,287 B1 * | 5/2002 | Dorner | A61B 6/00 378/154 |
| 7,626,174 B2 | 12/2009 | Schweizer | G01T 1/1648 250/370.09 |
| 8,000,435 B2 * | 8/2011 | Bertram | G06T 11/005 378/6 |
| 8,045,676 B2 * | 10/2011 | Hayashida | G01N 23/046 378/4 |
| 8,064,676 B2 * | 11/2011 | Li | A61B 6/00 382/132 |
| 8,326,011 B2 * | 12/2012 | Star-Lack | G06T 7/0012 378/7 |
| 8,674,313 B2 * | 3/2014 | Cao | G01T 1/2018 250/366 |
| 8,848,876 B2 * | 9/2014 | Kuwabara | A61B 6/4291 378/154 |
| 9,569,826 B2 * | 2/2017 | Naito | G06T 5/009 |
| 9,704,241 B2 * | 7/2017 | Imai | A61B 6/5282 |
| 9,719,947 B2 * | 8/2017 | Yun | G01N 23/20075 |
| 9,836,830 B2 * | 12/2017 | Naito | G01N 23/046 |
| 9,861,334 B2 * | 1/2018 | Tajima | A61B 6/5294 |
| 9,874,531 B2 * | 1/2018 | Yun | G01N 23/20075 |
| 9,877,696 B2 * | 1/2018 | Taki | A61B 6/4291 |
| 9,886,765 B2 * | 2/2018 | Naito | A61B 6/4291 |
| 9,918,692 B2 * | 3/2018 | Kawamura | A61B 6/461 |
| 9,947,101 B2 * | 4/2018 | Kawamura | A61B 6/466 |
| 9,978,132 B2 * | 5/2018 | Takahashi | G06T 5/008 |
| 9,980,696 B2 * | 5/2018 | Oda | A61B 6/465 |
| 10,045,746 B2 * | 8/2018 | Tajima | A61B 6/4233 |
| 10,058,301 B2 * | 8/2018 | Tajima | A61B 6/5282 |
| 10,080,541 B2 * | 9/2018 | Kawamura | A61B 6/461 |
| 10,098,603 B2 * | 10/2018 | Manak | A61B 6/5282 |
| 10,123,757 B2 * | 11/2018 | Tajima | A61B 6/04 |
| 10,136,873 B2 * | 11/2018 | Kawamura | A61B 6/5282 |
| 10,154,825 B2 * | 12/2018 | Enomoto | A61B 6/5282 |
| 10,172,583 B2 * | 1/2019 | Enomoto | A61B 6/4241 |
| 10,175,181 B2 * | 1/2019 | Cinquin | G21K 1/025 |
| 10,178,977 B2 * | 1/2019 | Kato | A61B 6/5205 |
| 10,194,881 B2 * | 2/2019 | Kawanishi | A61B 6/5282 |
| 10,219,770 B2 * | 3/2019 | Enomoto | A61B 6/463 |
| 10,231,688 B2 * | 3/2019 | Naito | A61B 6/588 |
| 10,258,305 B2 * | 4/2019 | Enomoto | A61B 6/4291 |
| 10,314,558 B2 * | 6/2019 | Noda | A61B 6/5282 |
| 10,349,908 B2 * | 7/2019 | Yun | A61B 6/4291 |
| 10,349,913 B2 * | 7/2019 | Enomoto | A61B 6/5282 |
| 10,359,375 B2 * | 7/2019 | Cao | H01J 35/14 |
| 2015/0379711 A1 | 12/2015 | Imai | |
| 2016/0140720 A1 | 5/2016 | Naito | |

FOREIGN PATENT DOCUMENTS

| | | |
|---|---|---|
| JP | 2014207958 | 11/2014 |
| JP | 2015043959 | 3/2015 |

OTHER PUBLICATIONS

Office Action of Japan Counterpart Application, with English translation thereof, dated Aug. 6, 2019, pp. 1-5.

* cited by examiner

FIG. 8

FOR ADULT

T1

| IMAGING REGION | IMAGING DIRECTION | DISTANCE [cm] | AVERAGE SUBJECT THICKNESS [cm] | RATIO OF SCATTERED RADIATION DOSE |
|---|---|---|---|---|
| CRANIUM | FRONT | 0 | 18 | 1.00 |
| CRANIUM | SIDE | 0 | 15 | 1.00 |
| CERVICAL SPINE | FRONT | 5 | 12 | 0.78 |
| CERVICAL SPINE | SIDE | 15 | 12 | 0.65 |
| CHEST | FRONT | 0 | 20 | 1.00 |
| ABDOMEN | FRONT | 0 | 22 | 1.00 |

FOR CHILD

T2

| IMAGING REGION | IMAGING DIRECTION | DISTANCE [cm] | AVERAGE SUBJECT THICKNESS [cm] | RATIO OF SCATTERED RADIATION DOSE |
|---|---|---|---|---|
| CRANIUM | FRONT | 0 | 13 | 1.00 |
| CRANIUM | SIDE | 0 | 12 | 1.00 |
| CERVICAL SPINE | FRONT | 3 | 9 | 0.93 |
| CERVICAL SPINE | SIDE | 10 | 9 | 0.82 |
| CHEST | FRONT | 0 | 15 | 1.00 |
| ABDOMEN | FRONT | 0 | 18 | 1.00 |

RADIATION IMAGE PROCESSING DEVICE, METHOD, AND PROGRAM CONFIGURED TO ELIMINATE SCATTERED RADIATION BASED ON A VIRTUAL GRID CHARACTERISTIC

CROSS REFERENCE TO RELATED APPLICATIONS

The present application claims priority under 35 U.S.C. § 119 to Japanese Patent Application No. 2016-122349 filed on Jun. 21, 2016. The above application is hereby expressly incorporated by reference, in its entirety, into the present application.

BACKGROUND

Field of the Invention

The present disclosure relates to a radiation image processing device, a method, and a program which perform processing for eliminating a scattered radiation component included in a radiation image.

Related Art

In the related art, when capturing a radiation image of a subject with radiation transmitted through the subject, if the thickness of the subject is particularly great, there is a problem in that radiation is scattered in the subject to cause scattered radiation and contrast of the acquired radiation image is degraded due to scattered radiation. For this reason, at the time of capturing a radiation image, a scattered radiation elimination grid (hereinafter, simply referred to as a grid) is disposed between the subject and a radiation detector such that the radiation detector which detects radiation to acquire a radiation image is not irradiated with scattered radiation, and imaging is performed. If imaging is performed using a grid, the radiation detector is hardly irradiated with radiation scattered by the subject, and thus, it is possible to improve contrast of the radiation image.

The grid has a configuration in which interspace materials, such as lead not transmitting radiation and aluminum or fiber easily transmitting radiation, are alternately disposed in a fine grating density of, for example, about 4.0 pieces/mm, and thus, is heavy. For this reason, in portable imaging which is performed in a patient's room or the like, the grid needs to be disposed between a patient lying on a bed and the radiation detector, and as a result, the burden of work to dispose and the burden of the patient at the time of imaging are great. In a case of a convergence type grid, concentration unevenness may occur in the radiation image due to oblique incidence of radiation. A fine stripe pattern (moire) corresponding to the pitch of the grid is recorded in the radiation image along with a subject mage, and the radiation image may be hard to view.

For this reason, a method in which capturing of a radiation image is performed without using a grid, and the effect of image quality improvement with elimination of scattered radiation by the grid is provided to the radiation image through image processing has been suggested (refer to JP2014-207958A). In the method of JP2014-207958A, the characteristics of a grid supposed to be used to eliminate scattered radiation at the time of capturing the radiation image are acquired, a scattered radiation component included in the radiation image is estimated based on the characteristics, and scattered radiation elimination processing is performed using the estimated scattered radiation component. Furthermore, a method in which a subject thickness distribution of a subject is estimated, a scattered radiation component is estimated using the estimated subject thickness distribution, and scattered radiation elimination processing is performed has been suggested (refer to JP2015-43959A).

SUMMARY

On the other hand, in the methods described in JP2014-207958A and JP2015-43959A, it is important to estimate the scattered radiation component with high accuracy. However, in actual imaging, there may be an air layer (air gap) between the subject and the radiation detector. If there is an air gap between the subject and the radiation detector, scattered radiation slips from a path of radiation to reach the radiation detector to the outside by a Groedel effect, and a scattered radiation dose reaching the radiation detector becomes small. In this way, in a situation in which the scattered radiation dose reaching the radiation detector becomes small, the scattered radiation dose estimated by the methods described in JP2014-207958A and JP2015-43959A becomes larger than the scattered radiation dose actually reaching the radiation detector. For this reason, in a situation in which there is an air gap, if the scattered radiation elimination processing is performed by the methods described in JP2014-207958A and JP2015-43959A, the scattered radiation component is excessively eliminated from the radiation image, and a radiation image is excessively enhanced in contrast.

JP2014-207958A describes that the scattered radiation elimination processing is performed in consideration of the air gap. However, how the air gap is considered is not specifically described in JP2014-207958A, and there is a demand for more specific scattered radiation elimination processing in consideration of an air gap.

The invention has been accomplished in consideration of the above-described situation, and an object of the invention is to allow a scattered radiation component to be eliminated from a radiation image with high accuracy in consideration of an air gap between a subject and a radiation detector.

A radiation image processing device according to the invention is a radiation image processing device which performs processing for eliminating scattered radiation included in radiation transmitted through a subject on a radiation image acquired by detecting radiation transmitted through the subject with a radiation detector, the radiation image processing device comprising imaging condition acquisition means for acquiring imaging conditions at the time of the acquisition of the radiation image, distance information acquisition means for acquiring distance information representing the distance between the subject and the radiation detector, scattered radiation information acquisition means for acquiring scattered radiation component information representing a scattered radiation component of radiation included in the radiation image based on at least the imaging condition, correction means for correcting the scattered radiation component information based on the distance information, and scattered radiation elimination means for performing scattered radiation elimination processing of the radiation image based on the corrected scattered radiation component information.

The "distance between the subject and the radiation detector" means a distance in a case where an imaging region to be imaged in the subject and the radiation detector are separated from each other and there is an air gap between the imaging region and the radiation detector. In detail, the "distance between the subject and the radiation detector" may be set as the distance between a portion in the imaging region closest to the radiation detector and the radiation detector. In a case where the imaging region and the radiation detector are in close contact with each other, the distance between the subject and the radiation detector becomes 0.

"Based on at least the imaging condition" means not only based on the imaging condition but also based on other kinds of information in addition to the imaging conditions. As other kinds of information, for example, at least one of subject information representing the type of a subject or grid information representing the type of a grid supposed to be used can be used.

In the radiation image processing device according to the invention, the imaging conditions may include at least one of the distance between a radiation source which irradiates the subject with the radiation and the radiation detector, the quality of the radiation, or the dose of the radiation.

In the radiation image processing device according to the invention, the correction means may acquire the ratio of the scattered radiation dose reaching the radiation detector according to the thickness of the subject and the distance information and may correct the scattered radiation component information based on the ratio.

The greater the distance between the subject and the radiation detector, the smaller the scattered radiation dose reaching the radiation detector by a Groedel effect. The "ratio of the scattered radiation dose" is the ratio of the scattered radiation dose reaching the radiation detector in a case where the ratio in a case where the distance between the subject and the radiation detector is 0 is set to 1.

In the radiation image processing device according to the invention, the distance information acquisition means may include a sensor for distance measurement and may acquire the distance information using the sensor.

In the radiation image processing device according to the invention, the distance information acquisition means may acquire the distance information based on an imaging region and an imaging direction of the subject.

In the radiation image processing device according to the invention, the distance information acquisition means may acquire the distance information with reference to a table in which the relationship between various imaging regions and various imaging directions, and the distance information is defined.

A radiation image processing method according to the invention is a radiation image processing method which performs processing for eliminating scattered radiation included in radiation transmitted through a subject on a radiation image acquired by detecting radiation transmitted through the subject with a radiation detector, the radiation image processing method comprising acquiring imaging conditions at the time of the acquisition of the radiation image, acquiring distance information representing the distance between the subject and the radiation detector, acquiring scattered radiation component information representing a scattered radiation component of radiation included in the radiation image based on at least the imaging condition, correcting the scattered radiation component information based on the distance information, and performing scattered radiation elimination processing of the radiation image based on the corrected scattered radiation component information.

The invention may be provided as a program which causes a computer to execute the radiation image processing method according to the invention.

According to the invention, the distance information representing the distance between the subject and the radiation detector is acquired, the scattered radiation component information acquired based on at least the imaging conditions is corrected according to the distance information, and the scattered radiation elimination processing of the radiation image is performed based on the corrected scattered radiation component information. Since the scattered radiation component information is acquired according to the distance information representing the distance between the subject and the radiation detector, the scattered radiation elimination processing taking an air gap into consideration is performed. Therefore, according to the invention, it is possible to perform the scattered radiation elimination processing with high accuracy in consideration of an air gap between the subject and the radiation detector.

BRIEF DESCRIPTION OF THE DRAWINGS

FIG. 8 is a diagram showing a table in which the relationship between various imaging regions and imaging directions, and the distance between the subject and the radiation detector is defined.

DETAILED DESCRIPTION

Figure 1:
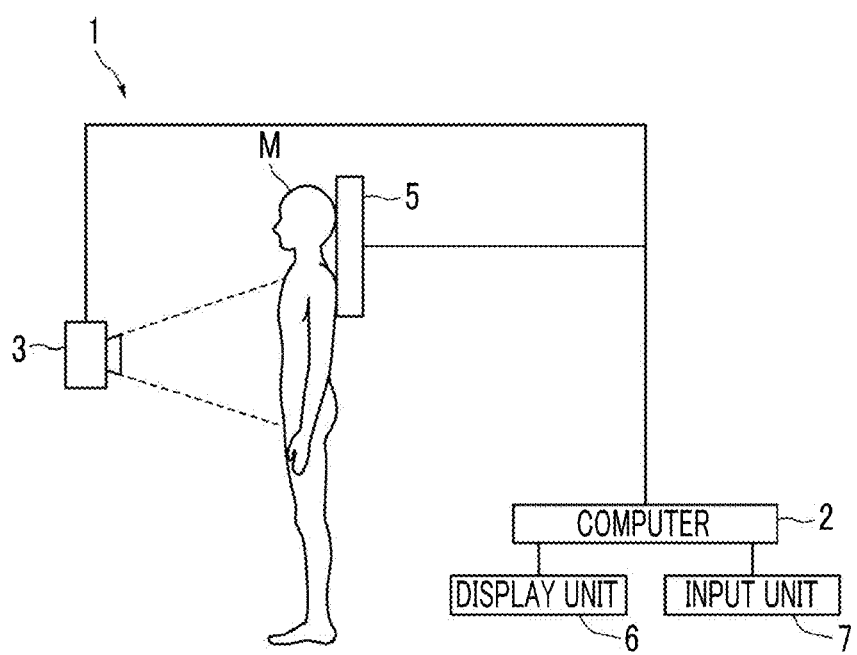
FIG. 1 is a schematic block diagram showing the configuration of a radiation imaging system to which a radiation image processing device according to a first embodiment of the invention is applied.

Hereinafter, an embodiment of the invention will be described referring to the drawings. FIG. 1 is a schematic block diagram showing the configuration of a radiation imaging system to which a radiation image processing device according to a first embodiment of the invention is applied. As shown in FIG. 1, the radiation imaging system according to the first embodiment performs various kinds of image processing including scattered radiation elimination processing on a radiation image of a subject, and as shown in FIG. 1, includes an imaging device 1, and a computer 2 including the radiation image processing device according to this embodiment.

The imaging device 1 includes an X-ray source 3 as a radiation source which irradiates a subject M with X-rays, and a radiation detector 5 which detects X-rays transmitted through the subject M to acquire a radiation image of the subject M.

The radiation detector 5 can repeatedly perform recording and reading of a radiation image, and a so-called direct radiation detector which is directly irradiated with radiation to generate electric charge may be used or a so-called indirect radiation detector which converts radiation to visible light once and converts visible light to an electric charge signal may be used. As a reading system of a radiation image signal, a so-called TFT reading system in which a radiation image signal is read by turning on and off a thin film transistor (TFT) switch, or a so-called optical reading system in which a radiation image signal is read by irradiation of reading light is desirably used; however, the invention is not limited thereto, and other systems may be used.

Figure 2:
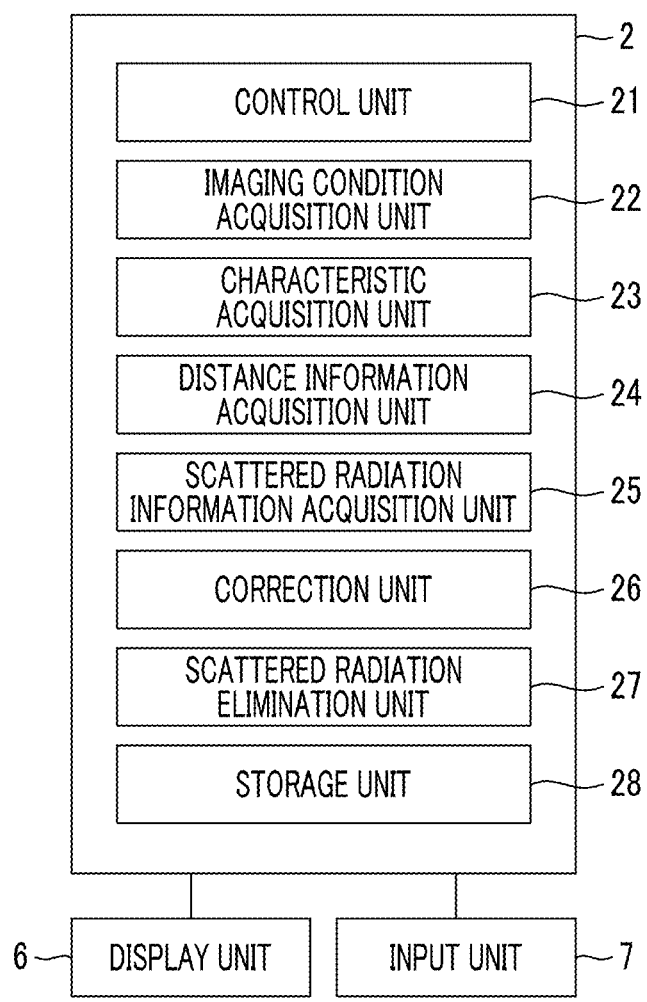
FIG. 2 is a block diagram showing the schematic configuration of a radiation imaging device in the first embodiment.

The computer 2 includes a central processing unit (CPU), a semiconductor memory, a communication interface, a storage device, such as a hard disk or an SSD, and the like, and as shown in FIG. 2, these kinds of hardware constitute a control unit 21, an imaging condition acquisition unit 22, a characteristic acquisition unit 23, a distance information acquisition unit 24, a scattered radiation information acquisition unit 25, a correction unit 26, a scattered radiation elimination unit 27, and a storage unit 28 of a radiation image processing device of the invention.

The control unit 21 performs control of imaging on the X-ray source 3 and the radiation detector 5, performs reading of a radiation image from the radiation detector 5, or performs control of entire processing which is performed in the computer 2.

The imaging condition acquisition unit 22 acquires imaging condition at the time of acquisition of a radiation image. The imaging conditions include at least one of the distance (SID (Source-to-Image Distance)) between the X-ray source 3 and the radiation detector 5, the quality of X-rays, or the dose of the X-rays, and may further include the material of a target of the X-ray source 3 and a filter, the type of the radiation detector 5, or the like.

Since the quality of the X-rays is defined by a tube voltage (kV) of the X-ray source 3 and a total filtration amount (mmAl eq. (amount of aluminum and the like)), the imaging condition acquisition unit 22 acquires the tube voltage and the total filtration amount. In a case where an additional filter made of copper or the like is used, a low energy component of X-rays is absorbed and a high energy component is increased. For this reason, in a case where the additional filter is used, information of the type of the additional filter is also acquired.

Since the dose of the X-rays is defined by a product (mAs) of a tube current (mA) of the X-ray source 3 and an irradiation time (s), the imaging condition acquisition unit 22 acquires the tube current and the irradiation time. In a case where an additional filter made of copper or the like is used, since a low energy component of X-rays is absorbed, the dose is decreased. For this reason, in a case where the additional filter is used, information of the type of the additional filter is also acquired.

The imaging condition acquisition unit 22 acquires the imaging conditions through an input from an input unit 7. The imaging condition acquisition unit 22 may acquire irradiation field information and subject information described below, in addition to the imaging conditions.

While the imaging conditions may be acquired by receiving an operator's input directly to the input unit 7, an input of the imaging conditions may be received by displaying a list of various imaging conditions on a display unit 6 and receiving selection of at least one of the imaging conditions from the list. The imaging conditions may be acquired from the X-ray source 3. In many cases, the imaging conditions are determined according to a facility where the radiation imaging system is installed. For this reason, the imaging conditions according to a facility may be stored in the storage unit 28, and the imaging conditions may be acquired from the storage unit 28.

In this embodiment, the radiation image processing device performs image processing on the radiation image such that the radiation image acquired by performing imaging without using a grid is given the same effect of eliminating the scattered radiation as in a case where imaging is performed actually using a grid. In this embodiment, for example, as described in JP2014-207958A and JP2015-43959A, scattered radiation elimination processing is performed based on a virtual grid characteristic. For this reason, the characteristic acquisition unit 23 acquires the virtual grid characteristic through an operator's input from the input unit 7. In this embodiment, it is assumed that the virtual grid characteristic is scattered radiation transmittance Ts about a virtual grid and transmittance (primary radiation transmittance) Tp of primary radiation transmitted through the subject M and directly irradiating the radiation detector 5. The scattered radiation transmittance Ts and the primary radiation transmittance Tp have values of 0 to 1.

While the characteristic acquisition unit 23 may acquire the virtual grid characteristic by directly receiving an input of the values of the scattered radiation transmittance Ts and the primary radiation transmittance Tp, in this embodiment, the virtual grid characteristic, that is, the scattered radiation transmittance Ts and the primary radiation transmittance Tp are acquired by receiving the designation of at least one of grid information representing the type of a grid, information (subject information) about the subject, or the imaging conditions at the time of the acquisition of the radiation image.

The grid information includes at least one of information for specifying the type of a grid, such as a grid ratio, grid density, a convergence type or a parallel type, a focusing distance in a case of a convergence type, and an interspace material (aluminum, fiber, BAKELITE, or the like). The scattered radiation transmittance Ts and the primary radiation transmittance Tp are different according to the type of a grid. For this reason, in regard to the grid information, a table in which at least one of various kinds of grid information is associated with the virtual grid characteristic is stored in the storage unit 28.

The subject information includes the type of a subject, such as chest, abdomen, or head (cranium and cervical spine). At the time of capturing a radiation image, in general, the type of a grid to be used is determined according to an imaging region, and the scattered radiation transmittance Ts and the primary radiation transmittance Tp are different according to the type of a grid. For this reason, in regard to the subject information, a table in which various kinds of subject information are associated with the virtual grid characteristic is stored in the storage unit 28.

The imaging conditions are acquired by the imaging condition acquisition unit 22. At the time of capturing a radiation image, in general, the type of a grid to be used is determined according to the imaging conditions, and the scattered radiation transmittance Ts and the primary radiation transmittance Tp are different according to the type of a grid. For this reason, in regard to the imaging conditions, a table in which various imaging conditions are associated with the virtual grid characteristic is stored in the storage unit 28.

The characteristic acquisition unit 23 acquires the virtual grid characteristic based on at least one of the grid information, the subject information, or the imaging conditions with reference to the tables stored in the storage unit 28. As the imaging conditions, those acquired by the imaging condition acquisition unit 22 may be used. While the grid information and the subject information may be acquired by an operator's input directly to the input unit 7, the grid information and the subject information may be acquired by displaying a list of various kinds of grid information and various kinds of subject information on the display unit 6 and receiving selection of at least one of grid information or subject information from the list.

In this embodiment, the scattered radiation elimination processing is performed by frequency resolution of the radiation image as described below. In this embodiment, the virtual grid characteristic is acquired for each of a plurality of frequency bands of the radiation image obtained by frequency resolution. For this reason, in the above-described table, the virtual grid characteristic is associated with each of a plurality of frequency bands.

A table in which all of the grid information, the subject information, and the imaging condition are associated with the virtual grid characteristic may be stored in the storage unit 28, and the virtual grid characteristic may be acquired based on all of the grid information, the subject information, and the imaging condition. In this case, the table becomes at least a four-dimensional table in which various kinds of grid information, various kinds of subject information, and various kinds of imaging conditions are associated with the virtual grid characteristic.

An exposure magnification factor which is an increase rate of an irradiation dose increasing with the use of a grid, a contrast improvement factor which is the ratio of contrast between a case where a grid is used and a case where a grid is not used, and selectivity which is the ratio of the primary radiation transmittance to the scattered radiation transmittance are characteristic values representing the characteristics of a grid, and the scattered radiation transmittance Ts and the primary radiation transmittance Tp can be calculated from these characteristic values. For this reason, in the characteristic acquisition unit 23, the virtual grid characteristic, that is, the scattered radiation transmittance Ts and the primary radiation transmittance Tp may be calculated and acquired by receiving the designation of at least one of the exposure magnification factor, the contrast improvement factor, or the selectivity.

The distance information acquisition unit 24 acquires distance information representing the distance between the subject M and the radiation detector. Specifically, the distance information representing a distance in a case where an imaging region to be imaged in the subject M and the radiation detector 5 are separated from each other and there is an air gap between the imaging region and the radiation detector 5 is acquired.

Figure 3:
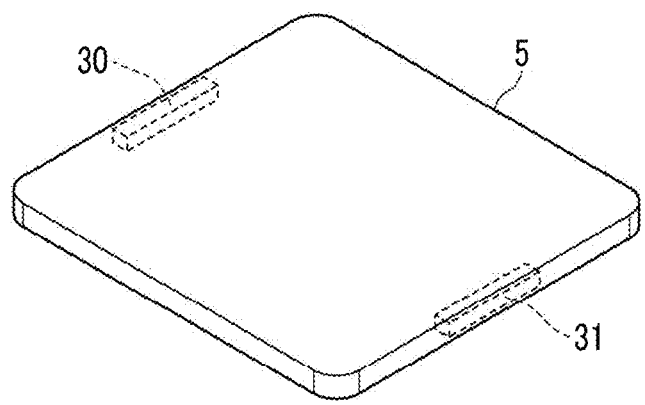
FIG. 3 is a diagram showing the configuration of a radiation detector including a sensor for acquiring distance information.
Figure 4:
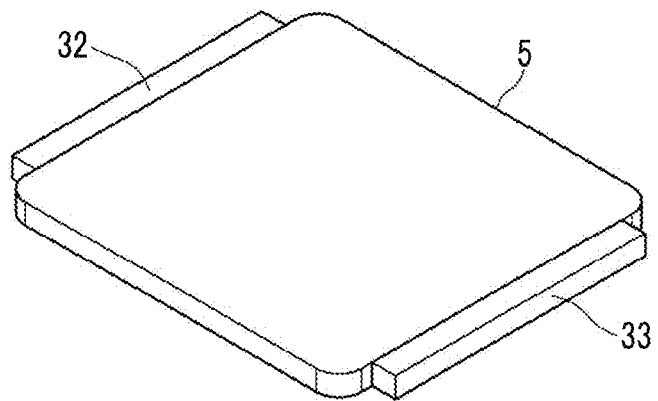
FIG. 4 is a diagram showing another configuration of a radiation detector including a sensor for acquiring distance information.

FIG. 3 is a diagram showing the configuration of a radiation detector 5 including a sensor for acquiring distance information. As shown in FIG. 3, sensors 30 and 31 for distance measurement are housed near two opposing sides in a housing of the radiation detector 5. As shown in FIG. 4, sensors 32 and 33 which are attachable to and detachable from the two opposing sides of the radiation detector 5 may be provided. As the sensors for distance measurement, ultrasonic sensors using ultrasonic waves, optical sensors using laser light, or the like can be used.

Figure 5:
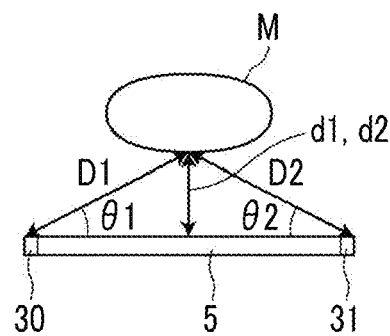
FIG. 5 is a diagram illustrating a measurement of a distance using a sensor for distance measurement.

FIG. 5 is a diagram illustrating a measurement of a distance using sensors for distance measurement. In FIG. 5, the sensors 30 and 31 housed in the housing of the radiation detector 5 shown in FIG. 3 are used. At the time of imaging, an imaging region of the subject M is disposed near the center of the radiation detector 5. For this reason, first, the distances D1 and D2 between the sensors 30 and 31 and the central portion of the subject M are measured by the sensors 30 and 31. Measurement directions $\theta 1$ and $\theta 2$ of the sensors 30 and 31 are also acquired by the sensors 30 and 31. The distance information acquisition unit 24 calculates the distance information representing the distance between the subject M and the radiation detector 5 from the acquired distances D1 and D2 and the measurement directions $\theta 1$ and $\theta 2$. That is, first distance information d1 is calculated from the distance D1 and the measurement direction $\theta 1$ by $d1 = D1 \times \sin \theta 1$, and second distance information d2 is calculated from the distance D2 and the measurement direction $\theta 2$ by $d2 = D2 \times \sin \theta 2$. Then, an average value of the first and second distance information d1 and the second distance information d2 is acquired as distance information. It should be noted that only the distance D1 and the measurement direction $\theta 1$ may be acquired to calculate only the first distance information d1, or only the distance D2 and the measurement direction $\theta 2$ may be acquired to calculate only the second distance information d2.

In this embodiment, the scattered radiation elimination processing is performed based on scattered radiation component information as well as the virtual grid characteristic. For this reason, the scattered radiation information acquisition unit 25 acquires the scattered radiation component information based on at least the imaging conditions.

The correction unit 26 corrects the scattered radiation component information based on the distance information.

The scattered radiation elimination unit 27 performs the scattered radiation elimination processing of the radiation image based on the corrected scattered radiation component information.

The storage unit 28 stores various kinds of information necessary for the scattered radiation elimination processing to be performed in the computer 2.

The display unit 6 is constituted of a CRT, a liquid crystal display, or the like, and assists various inputs necessary for the radiation image acquired by imaging and the scattered radiation elimination processing. The input unit 7 is constituted of a keyboard, mouse, a touch panel, and the like.

The processing which is performed in the control unit 21, the imaging condition acquisition unit 22, the characteristic acquisition unit 23, the distance information acquisition unit 24, the scattered radiation information acquisition unit 25, the correction unit 26, and the scattered radiation elimination unit 27 is performed by a central processing unit with a computer program stored in the storage unit 28. A plurality of processing devices or processing circuits which perform the respective processing of the respective units may be provided in the computer 2.

Figure 6:
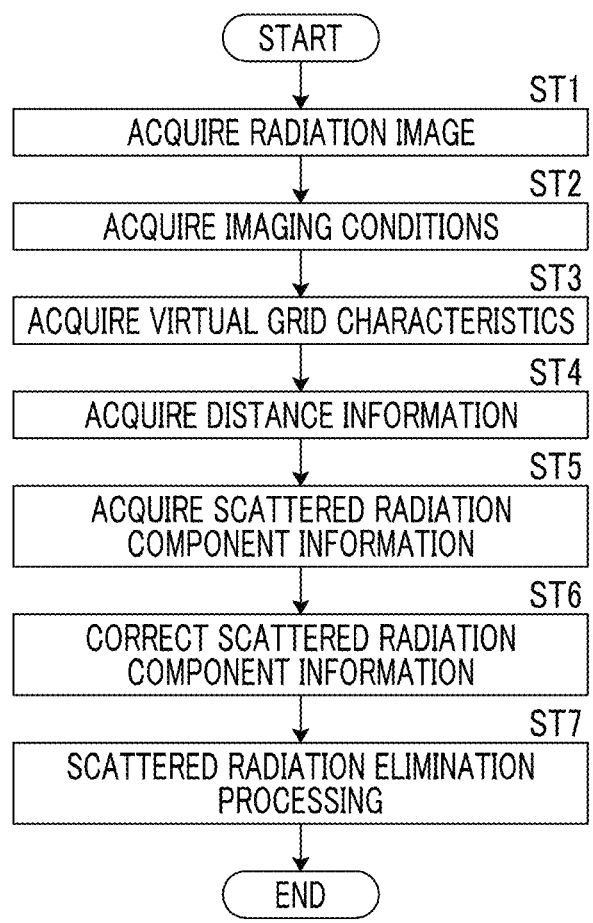
FIG. 6 is a flowchart showing processing which is performed in the first embodiment.

Next, processing which is performed in the first embodiment will be described. FIG. 6 is a flowchart showing processing which is performed in the first embodiment.

Imaging of the subject M is performed and the control unit 21 of the computer 2 acquires the radiation image (Step ST1). The imaging condition acquisition unit 22 acquires the imaging conditions (Step ST2), the characteristic acquisition unit 23 acquires the virtual grid characteristic (Step ST3), and the distance information acquisition unit 24 acquires the distance information representing the distance between the subject M and the radiation detector 5 (Step ST4). It should be noted that the processing of Steps ST2 to ST4 may be performed in an arbitrary order and may be performed earlier than Step ST1, or may be performed in parallel with Step ST1.

Next, the scattered radiation information acquisition unit 25 acquires the scattered radiation component information representing a scattered radiation component of radiation included in the radiation image (Step ST5). Specifically, the scattered radiation information acquisition unit 25 analyzes the radiation image to acquire a scattered radiation content distribution, which is the distribution of scattered radiation in the radiation image, as the scattered radiation component information. The analysis of the radiation image is performed based on irradiation field information, the subject information, and the imaging conditions at the time of capturing the radiation image.

The irradiation field information is information representing an irradiation field distribution relating to the position and size of an irradiation field included in the radiation image in a case where imaging is performed using an irradiation field diaphragm. The subject information is, for example, the imaging region of the subject M, such as cervical spine, head, chest, or abdomen, and information relating to the position of the subject M on the radiation image, the distribution of the composition of the subject M, the size of the subject M, the thickness of the subject M, and the like. The imaging conditions are acquired by the above-described imaging condition acquisition unit 22. The irradiation field information, the subject information, and the imaging conditions are factors for determining the distribution of scattered radiation included in the radiation image. For example, the amount of scattered radiation depends on the magnitude of the irradiation field, and the greater the thickness of the subject, the greater the amount of scattered radiation. Accordingly, with the use of these kinds of information, it is possible to acquire the scattered radiation content distribution more accurately.

The scattered radiation information acquisition unit 25 calculates a primary radiation component and a scattered radiation component from a distribution $T(x,y)$ of a subject thickness in the radiation image acquired by imaging according to Expressions (1) and (2) described below, and calculates a scattered radiation content distribution $S(x,y)$ as the scattered radiation component information from the calculated primary radiation component and scattered radiation component based on Expression (3). The scattered radiation content distribution $S(x,y)$ has a value of 0 to 1. The subject thickness means the total sum of the thickness of a subject area excluding an air area on a path of irradiated radiation.

$$Ip(x,y) = Io(x,y) \times \exp(-\mu \times T(x,y)) \quad (1)$$

$$Is(x,y) = Io(x,y) * S\sigma(T(x,y)) \quad (2)$$

$$S(x,y) = Is(x,y)/(Is(x,y) + Ip(x,y)) \quad (3)$$

Here, $(x,y)$ is the coordinates of a pixel position of the radiation image, $Ip(x,y)$ is a primary radiation component at the pixel position $(x,y)$, $Is(x,y)$ is a scattered radiation component at the pixel position $(x,y)$, $Io(x,y)$ is an incidence dose to the subject surface at the pixel position $(x,y)$, $\mu$ is a radiation attenuation coefficient of the subject, $S\sigma(T(x,y))$ is a convolution kernel representing the characteristics of scattering according to the subject thickness at the pixel position $(x,y)$. Expression (1) is an expression based on a known exponential attenuation rule, and Expression (2) is an expression based on a method described in "J M Boon et al, An analytical model of the scattered radiation distribution in diagnostic radiolog, Med. Phys. 15(5), September/October 1988" (Reference Document 1). Even if the incidence dose $Io(x,y)$ to the subject surface is defined as any value, the incidence dose $Io(x,y)$ is cancelled by division when calculating $S(x,y)$, and thus, the incidence dose $Io(x,y)$ may be set to an arbitrary value, for example, 1 or the like.

The distribution $T(x,y)$ of the subject thickness may be calculated by assuming that a brightness distribution in the radiation image substantially matches the distribution of the thickness of the subject and converting a pixel value of the radiation image to the thickness with the radiation attenuation coefficient value. In place of this, the thickness of the subject may be measured using a sensor or the like, or may be approximated by a model, such as a cube or an elliptic cylinder.

In Expression (2), * is an operator representing a convolution operation. The property of a kernel changes depending on the distribution of the irradiation field, the distribution of the composition of the subject, the irradiation dose at the time of imaging, the tube voltage, an imaging distance, the characteristics of the radiation detector, and the like, in addition to the thickness of the subject. According to the method described in Reference Document 1, scattered radiation can be approximated by convolution of a point spread function (in Expression (2), $S\sigma(T(x,y))$) to primary radiation. $S\sigma(T(x,y))$ can be obtained experimentally according to the irradiation field information, the subject information, the imaging conditions, and the like.

In this embodiment, while $S\sigma(T(x,y))$ may be calculated based on the irradiation field information, the subject information, and the imaging condition at the time of imaging, a table in which various kinds of irradiation field information, various kinds of subject information, and various imaging conditions are associated with $S\sigma(T(x,y))$ may be stored in the storage unit 28, and $S\sigma(T(x,y))$ may be obtained based on the irradiation field information, the subject information, and the imaging conditions at the time of imaging with reference to the table. $S\sigma(T(x,y))$ may be approximated by $T(x,y)$.

Figure 7:
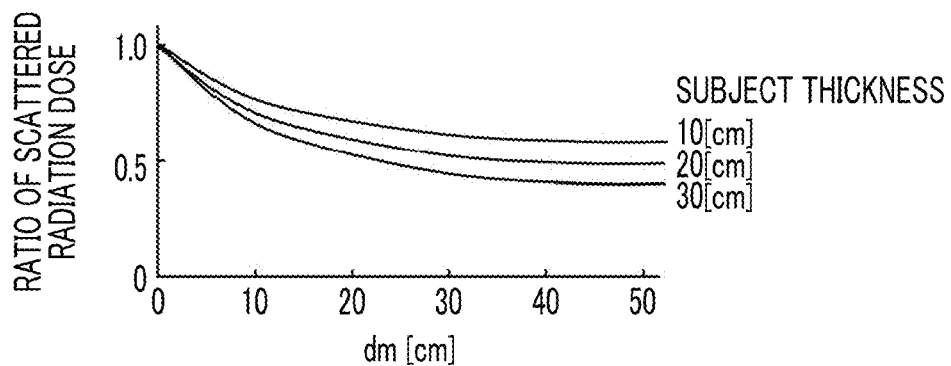
FIG. 7 is a diagram showing the relationship between distance information and a ratio of a scattered radiation dose according to the thickness of a subject.

The correction unit 26 corrects the scattered radiation component information based on the distance information (Step ST6). Specifically, $S(x,y)$ calculated by Expression (3) described above is corrected based on the distance information. FIG. 7 is a diagram showing the relationship between distance information and a ratio of a scattered radiation dose according to the thickness of the subject M. In FIG. 7, the horizontal axis indicates the distance between the subject M and the radiation detector 5, and the vertical axis indicates the ratio of the scattered radiation dose. The ratio of the scattered radiation dose is the ratio of the scattered radiation dose reaching the radiation detector 5 in a case where the ratio in a case where the distance between the subject M and the radiation detector 5 is 0 is set to 1. As shown in FIG. 7, the greater the distance represented by the distance information, the greater a decrease rate of scattered radiation, and the smaller the ratio of the scattered radiation dose reaching the radiation detector 5. The greater the subject thickness, the greater the decrease rate of scattered radiation, and the smaller the ratio of the scattered radiation dose. The greater the distance, the smaller change in the decrease rate of scattered radiation and the smaller the degree of decrease of the ratio of the scattered radiation dose, and if the distance exceeds about 40 cm, the ratio of scattered radiation dose becomes substantially constant. In this embodiment, the relationship shown in FIG. 7 is stored in the storage unit 28 in the form of a table. The correction unit 26 acquires the ratio C of the scattered radiation dose from the distance information and the distribution T(x,y) of the subject thickness with reference to the table representing the relationship shown in FIG. 7, and multiplies S(x,y) by the ratio C to acquire the corrected scattered radiation component information, that is, the corrected scattered radiation content distribution Sh(x,y) by Expression (4) described below. In the relationship shown in FIG. 7, three relationships between the distance information and the ratio of the scattered radiation dose according to the thickness of the subject M in a case where the subject thickness is 10 cm, 20 cm, and 30 cm are shown. For this reason, in regard to an intermediate subject thickness of these subject thicknesses, the ratio C may be calculated by linearly interpolating the ratios obtained from the three relationships.

$$Sh(x,y) = C \times S(x,y) \tag{4}$$

The ratio C may be acquired based on the subject thickness distribution T(x,y) for each pixel position (x,y), or an average value of the subject thickness distribution T(x,y) for the entire image may be calculated and only one ratio C may be acquired based on the average value.

Next, the scattered radiation elimination unit 27 performs the scattered radiation elimination processing by reducing the frequency components of the frequency bands regarded as scattered radiation in the radiation image based on the corrected scattered radiation component information (Step ST7). For this reason, the scattered radiation elimination unit 27 performs frequency resolution of the radiation image to acquire a frequency component of each of a plurality of frequency bands, performs processing for reducing a gain of at least one frequency component, and synthesizes the processed frequency component and other frequency components to acquire a radiation image subjected to the scattered radiation elimination processing. As a method of frequency resolution, in addition to a method of performing multiresolution transform on the radiation image, known arbitrary methods, such as wavelet transform and Fourier transform, can be used.

The scattered radiation elimination unit 27 calculates a conversion coefficient R(x,y) for converting a frequency component from the scattered radiation transmittance Ts and the primary radiation transmittance Tp as the virtual grid characteristic, and the corrected scattered radiation content distribution Sh(x,y) by Expression (5) described below.

$$R(x,y) = Sh(x,y) \times Ts + (1-Sh(x,y)) \times Tp \tag{5}$$

Since the scattered radiation transmittance Ts and the primary radiation transmittance Tp, and the corrected scattered radiation content distribution Sh(x,y) have values of 0 to 1, the conversion coefficient R(x,y) also has a value of 0 to 1. The scattered radiation elimination unit 27 calculates the conversion coefficient R(x,y) for each of a plurality of frequency bands.

In the following description, the pixel value of the radiation image is represented by I(x,y), a frequency component image obtained by frequency resolution is represented by I(x,y,r), frequency synthesis is represented by I(x,y)=ΣrI(x,y,r), the conversion coefficient of each frequency band is represented by R(x,y,r), and the scattered radiation transmittance and the primary radiation transmittance of each frequency band are represented by as Ts(r) and Tp(r). r represents the layer of the frequency band, and the greater r, the lower the frequency. Accordingly, I(x,y,r) becomes a frequency component image of a certain frequency band. While the corrected scattered radiation content distribution Sh(x,y) about the radiation image may be used as it is, similarly to the scattered radiation transmittance Ts and the primary radiation transmittance Tp, the scattered radiation content distribution Sh(x,y) may be acquired for each frequency band.

In this embodiment, the conversion coefficient R(x,y,r) is calculated for each frequency component, the pixel value of the frequency component image I(x,y,r) is converted by multiplying the frequency component image I(x,y,r) by the conversion coefficient R(x,y,r) of the corresponding frequency band, and the frequency component image I(x,y,r) (that is, I(x,y,r)×R(x,y,r)) multiplied by the conversion coefficient R(x,y,r) is frequency-synthesized to acquire a processed radiation image I'(x,y). Accordingly, the processing which is performed in the scattered radiation elimination unit 27 is represented by Expression (6) described below. Since the conversion coefficient R(x,y,r) has a value of 0 to 1, the pixel value of the frequency component at the pixel position (x,y), that is, the gain is reduced by multiplying the frequency component (x,y,r) by the conversion coefficient R(x,y,r) of the corresponding frequency band.

$$\begin{aligned} I'(x,y) &= \sum r\{I(x,y,r) \times R(x,y,r)\} \\ &= \sum r\{I(x,y,r) \times (Sh(x,y) \times Ts(r) + \\ &\quad (1-Sh(x,y)) \times Tp(r))\} \end{aligned} \tag{6}$$

In this embodiment, it is assumed that the radiation image is frequency-resolved into six frequency bands, and the scattered radiation transmittance Ts and the primary radiation transmittance Tp are acquired for the six frequency bands. In this case, the scattered radiation transmittance Ts and the primary radiation transmittance Tp have, for example, values shown in Expression (7) described below. In Expression (7), it is assumed that the value represents a lower frequency band toward the right side.

$$Ts=\{0.7,0.7,0.7,0.7,0.3,0.2\}$$

$$Tp=\{0.7,0.7,0.7,0.7,0.7,0.7\} \tag{7}$$

As shown in (7), while the scattered radiation transmittance Ts and the primary radiation transmittance Tp have the same value in a high frequency band (r=1 to 4), in a low frequency band (r=5 to 6), the scattered radiation transmittance Ts has a lower value. This is because a grid has a high elimination rate in a low frequency band, in which the frequency component of scattered radiation is dominant, but has small frequency dependence of the elimination rate for primary resolution.

The value of conversion coefficient calculated based on Expressions (5) and (7) becomes smaller in an area in the radiation image where the content of the scattered radiation is higher. Accordingly, in the processed radiation image acquired by performing the processing shown in Expression (6) using the conversion coefficient calculated in this way, a scattered radiation component is eliminated according to the type of a grid supposed to be used and the air gap as the distance between the subject M and the radiation detector 5.

The scattered radiation elimination unit 27 may eliminate scattered radiation of the radiation image as follows. First, as above, if frequency synthesis is represented by I(x,y)=ΣrI (x,y,r), the scattered radiation elimination unit 27 resolves the frequency component image I(x,y,r) into the scattered radiation component Is(x,y,r) and the primary radiation component Ip(x,y,r) using the scattered radiation content distribution S(x,y) by Expression (8) described below.

$$Is(x,y,r)=Sh(x,y)\times I(x,y,r)$$

$$Ip(x,y,r)=(1-Sh(x,y))\times I(x,y,r) \quad (8)$$

The scattered radiation elimination unit 27 performs image conversion by applying the scattered radiation transmittance Ts(r) and the primary radiation transmittance Tp(r) as the virtual grid characteristic respectively to the scattered radiation component Is(x,y,r) and the primary radiation component Ip(x,y,r) by Expression (9) described below, and calculates converted scattered radiation component Is'(x,y,r) and primary radiation component Ip'(x,y,r).

$$Is'(x,y,r)=Is(x,y,r)\times Ts(r)=Sh(x,y)\times I(x,y,r)\times Ts(r)$$

$$Ip'(x,y,r)=Ip(x,y,r)\times Tp(r)=(1-Sh(x,y))\times I(x,y,r)\times Tp(r) \quad (9)$$

Is'(x,y,r) and the primary radiation component Ip'(x,y,r) are frequency-synthesized by Expression (10) described below to calculate the processed radiation image I'(x,y).

$$\begin{aligned}I'(x,y) &= \sum r\{Is'(x,y,r)+Ip'(x,y,r)\} \quad (10)\\ &= \sum r\{Sh(x,y)\times I(x,y,r)\times Ts(r)+\\ &\quad (1-Sh(x,y))\times I(x,y,r)\times Tp(r)\}\\ &= \sum r\{I(x,y,r)\times(Sh(x,y)\times Ts(r)+\\ &\quad (1-Sh(x,y))\times Tp(r))\}\end{aligned}$$

In this way, in the first embodiment, the scattered radiation component information, that is, the scattered radiation transmittance distribution is corrected according to the distance information representing the distance between the subject M and the radiation detector 5, and the scattered radiation elimination processing of the radiation image is performed based on the corrected scattered radiation component information. Since the scattered radiation component information is acquired according to the distance information representing the distance between the subject M and the radiation detector 5, the scattered radiation elimination processing taking the air gap into consideration is performed. Therefore, according to this embodiment, it is possible to perform the scattered radiation elimination processing with high accuracy in consideration of the air gap between the subject M and the radiation detector 5.

In the first embodiment, the distance information is acquired using the sensors for distance measurement in the distance information acquisition unit 24. However, a table in which the relationship between various imaging regions and imaging directions, and the distance between the subject M and the radiation detector 5 is defined may be stored in the storage unit 28, and the distance information may be acquired by receiving an input of the imaging region and the imaging direction from the input unit 7 with reference to the table. FIG. 8 is a diagram showing a table in which the relationship between various imaging regions and imaging directions, and the distance between the subject M and the radiation detector 5 is defined. In FIG. 8, the distance between the subject M and the radiation detector 5 is simply referred to as "distance". As shown in FIG. 8, a table T1 defines the relationship between various imaging regions and imaging directions, and the distance between the subject M and the radiation detector 5. In the table T1, an average subject thickness and a ratio of a scattered radiation dose to various imaging regions and imaging directions are also defined. Since the distance and the average subject thickness are different between a case where the subject M is an adult and a case where the subject M is a child, in addition to the table T1 for adult, a table T2 for child is also stored in the storage unit 28.

The distance information acquisition unit 24 can acquire the distance between the subject M and the radiation detector 5 by storing the tables T1 and T2 in the storage unit 28 and receiving an input of the imaging region and the imaging direction from the input unit 7. For example, in a case where the imaging region is a lateral cervical spine of the subject M of the adult, the distance becomes 15 cm. With this, since the sensors for distance measurement are not required, it is possible to make the configuration of the radiation image processing device simple and inexpensive. The average subject thickness included in the tables T1 and T2 can be used as the distribution T(x,y) of the subject thickness. The ratio C of the scattered radiation dose can also be acquired from the tables T1 and T2.

In the tables T1 and T2, the ratio of the scattered radiation dose may not be included. In this case, the distance, that is, the distance information may be acquired with reference to the tables T1 and T2, and the ratio C of the scattered radiation dose may be acquired based on the distance information with reference to the table in which the relationship shown in FIG. 7 is defined.

Figure 9:
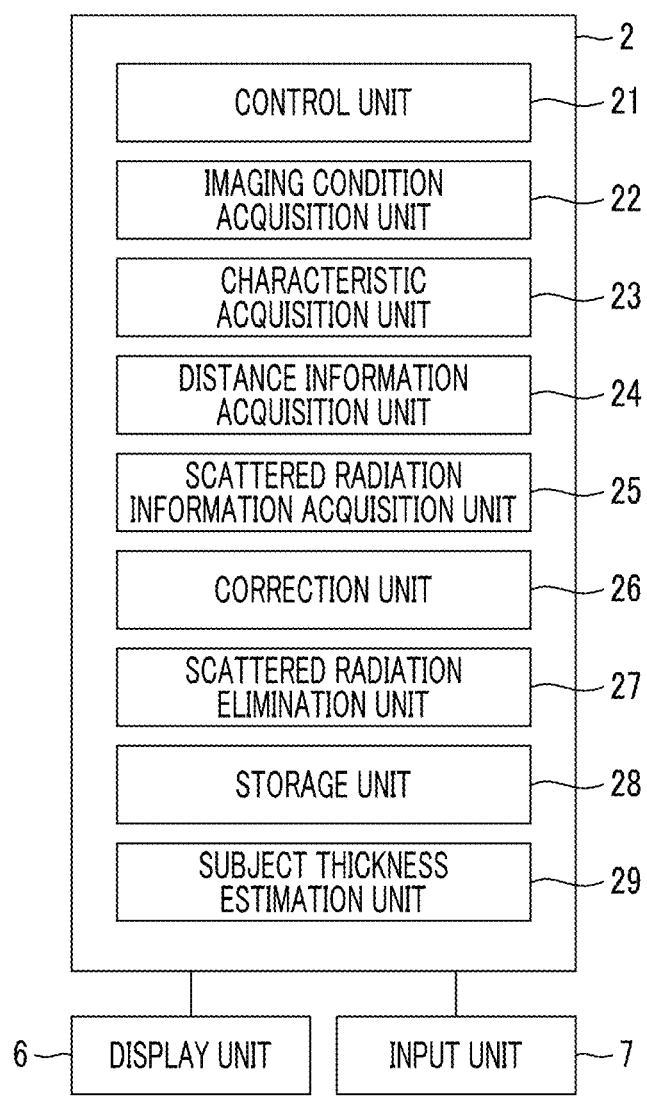
FIG. 9 is a block diagram showing the schematic configuration of a radiation imaging device in a second embodiment.

In the above-described first embodiment, the subject thickness distribution of the subject M may be estimated using the method described in JP2015-43959A, and the scattered radiation component information may be acquired using the estimated subject thickness distribution. Hereinafter, the estimation of the subject thickness distribution will be described as a second embodiment of the invention. FIG. 9 is a block diagram showing the schematic configuration of a radiation imaging device according to the second embodiment. As shown in FIG. 9, the second embodiment is different from the first embodiment in that a subject thickness estimation unit 29 which analyzes the radiation image to estimate the subject thickness distribution of the subject M is provided.

Figure 10:
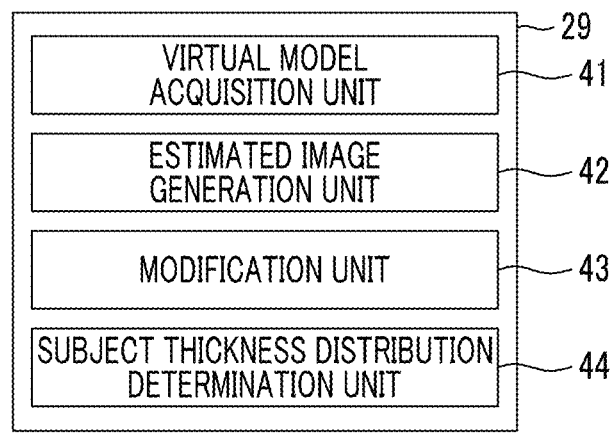
FIG. 10 is a schematic block diagram showing the configuration of a subject thickness estimation unit.

FIG. 10 is a schematic block diagram showing the configuration of the subject thickness estimation unit. As shown in FIG. 10, the subject thickness estimation unit 29 includes a virtual model acquisition unit 41, an estimated image generation unit 42, a modification unit 43, and a subject thickness distribution determination unit 44.

The virtual model acquisition unit 41 acquires a virtual model K of the subject M having an initial subject thickness distribution T0 (predetermined subject thickness distribution).

The estimated image generation unit 42 generates an image, in which an estimated primary radiation image Ip estimating a primary radiation image obtained by radiography from the virtual model and an estimated scattered radiation image Igs estimating a scattered radiation image obtained by radiography from the virtual model are synthesized, based on the virtual model K as an estimated image Im estimating a radiation image obtained by radiography from the subject M.

The modification unit 43 modifies the initial subject thickness distribution T0 of the virtual model K based on the estimated image Im and the radiation image such that the difference between the estimated image Im and the radiation image becomes small.

The subject thickness distribution determination unit 44 determines a modified subject thickness distribution Tn−1 (where n is a natural number) to a subject thickness distribution Tk of the radiation image.

In the second embodiment, the virtual model K of the subject M having the initial subject thickness distribution T0(x,y) is stored in the storage unit 28.

Figure 11:
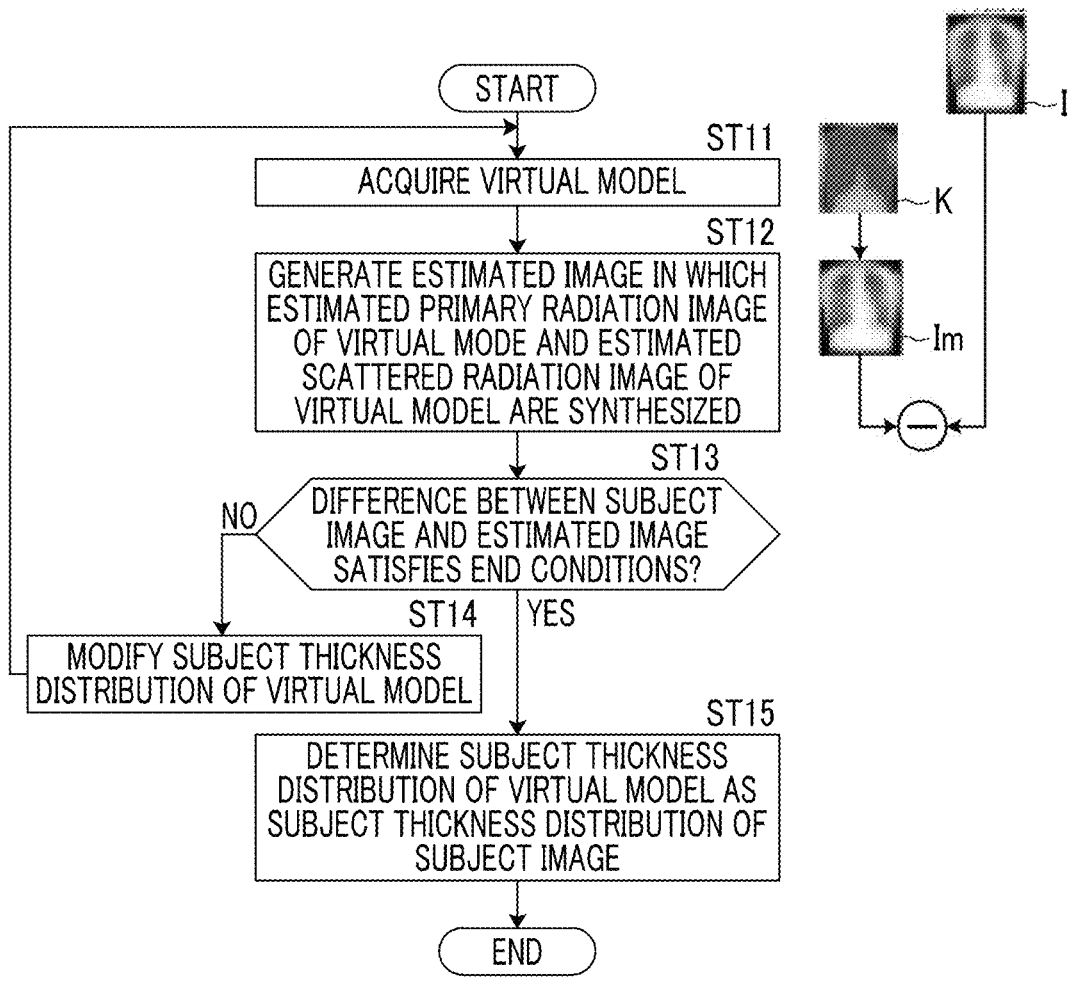
FIG. 11 is a flowchart of subject thickness estimation processing.

FIG. 11 is a flowchart of subject thickness estimation processing. The virtual model acquisition unit 41 of the subject thickness estimation unit 29 acquires the virtual model K of the subject M having the initial subject thickness distribution T0(x,y) from the storage unit 28 (Step ST11). The virtual model K is data virtually representing the subject M with the subject thickness according to the initial subject thickness distribution T0(x,y) associated with each position on an xy plane. Structures (anatomical structures, such as bones and organs) included in the virtual model K, the arrangement of the structures, and characteristic information indicating characteristics or the like of the structures to radiation are set based on the arrangement and composition of anatomical structures, such as bones and organs, of a subject for comparison.

Figure 12:
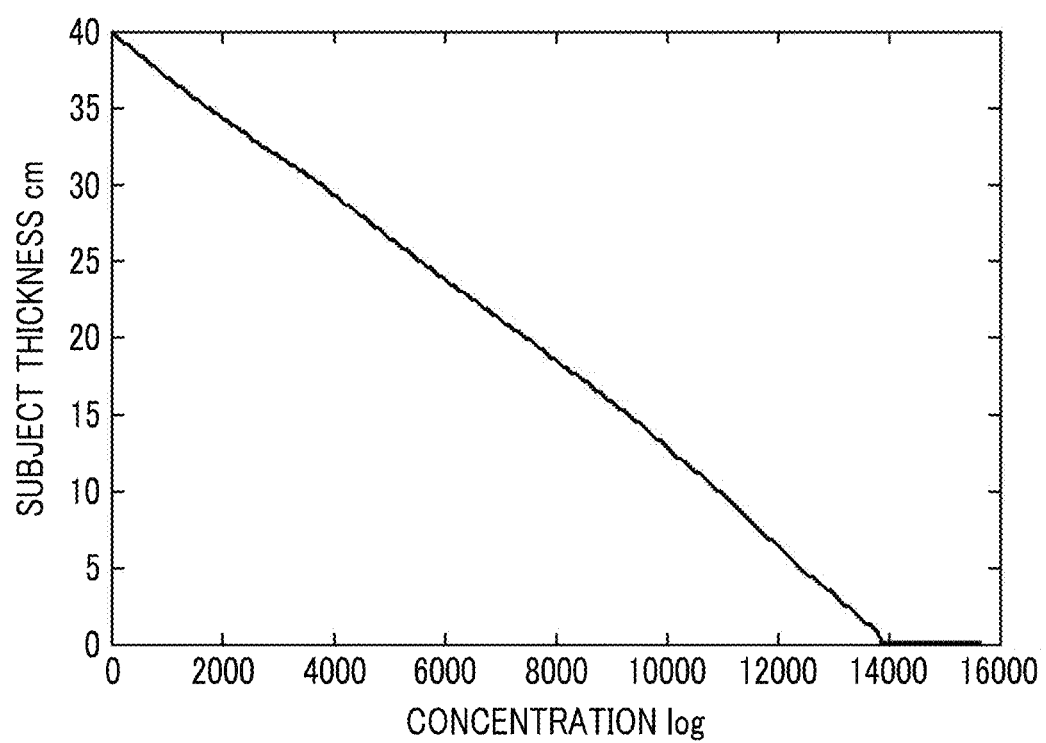
FIG. 12 is a diagram showing an example of an association table of a subject thickness distribution.

While the initial subject thickness distribution T0(x,y) of the virtual model K may have an arbitrary distribution, in this embodiment, the initial subject thickness distribution T0 is generated and acquired by the virtual model acquisition unit 41. The virtual model acquisition unit 41 acquires the imaging conditions, such as the imaging dose of the subject M, the tube voltage, and SID, and acquires a table, in which the pixel value and the subject thickness according to the imaging conditions of the subject M are associated with each other, from the storage unit 28. The imaging conditions are the imaging conditions acquired by the imaging condition acquisition unit 22. FIG. 12 shows an example of a table in which the pixel value is associated with the subject thickness. Then, the virtual model acquisition unit 41 acquires the subject thickness distribution of the radiation image by specifying the subject thickness corresponding to the pixel value of each pixel of the radiation image of the subject M based on the table shown in FIG. 12. Then, the virtual model acquisition unit 41 acquires the subject thickness distribution of the radiation image as the initial subject thickness distribution T0 (predetermined subject thickness distribution) of the virtual model K. The initial subject thickness distribution T0 may be generated during the acquisition processing of the virtual model K as in this embodiment, or may be set in advance prior to the acquisition processing of the virtual model K. The above processing is represented by Expression (11) described below. I(x,y) indicates the pixel value of each pixel in the radiation image, and T0(x,y) indicates the initial subject thickness distribution at each pixel position.

$$T_0(x,y) = \text{LUT}(I(x,y)) \quad (11)$$

Figure 13:
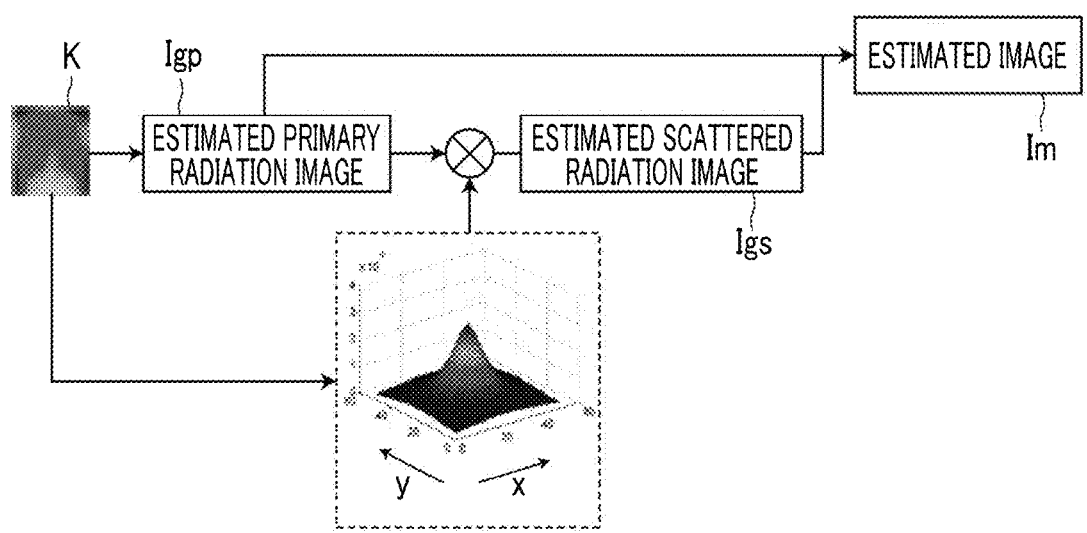
FIG. 13 is a diagram illustrating an example of a method of generating an estimated image.
Figure 14:
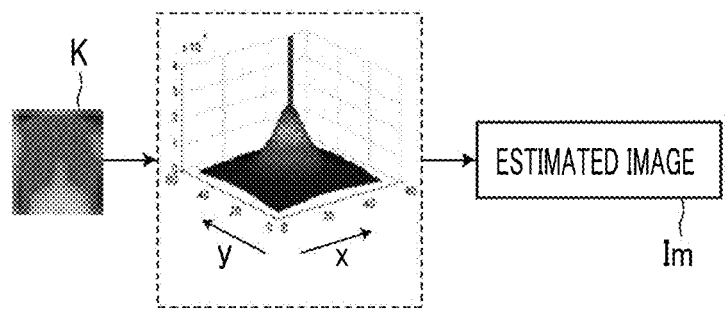
FIG. 14 is a diagram illustrating another example of a method of generating an estimated image.

Next, the estimated image generation unit 42 generates the estimated image Im in which the estimated primary radiation image Igp obtained in a case of imaging the virtual model K under the same imaging conditions as the radiation image and the estimated scattered radiation image Igs obtained in a case of imaging the virtual model K under the same imaging conditions as the radiation image are synthesized (Step ST12). FIGS. 13 and 14 are diagrams illustrating a method of generating the estimated image Im.

As shown in FIG. 13, the estimated image generation unit 42 generates the estimated primary radiation image Igp obtained in a case of imaging the virtual model K under the same imaging conditions as the radiation image according to Expression (12) described below, and generates the estimated scattered radiation image Igs using the generated estimated primary radiation image Igp according to Expression (13). Then, as shown in Expression (14), the estimated image generation unit 42 synthesizes the estimated primary radiation image Igp and the estimated scattered radiation image Igs to generate the estimated image Im (Step ST12). When creating the estimated primary radiation image Igp and the estimated scattered radiation image Igs at the first time, the initial subject thickness distribution T0(x,y) is used in Estimation Expression (12) and Expression (13) (in Expressions (12) and (13), n=1).

$$I_{gp}(x, y) = I_o(x, y) \times \exp(-T_{n-1}(x, y) \times \mu) \quad (12)$$

$$I_{gs}(x, y) = \sum_{x',y'} I_{gp}(x', y') K_s(x, y, T_{n-1}(x', y'), \theta_{x',y'}) \quad (13)$$

$$I_m(x, y) = I_{gp}(x, y) + I_{gs}(x, y) \quad (14)$$

Here, (x,y) is the coordinates of the pixel position of the radiation image, Igp(x,y) is an estimated primary radiation image at the pixel position (x,y), Igs(x,y) is an estimated scattered radiation image at the pixel position (x,y), Io(x,y) is a dose at the pixel position (x,y), Im(x,y) is an estimated image at the pixel position (x,y), μ is a radiation attenuation coefficient of the subject, and Ks(x,y,Tn(x',y'),θx',y') is a convolution kernel representing a point spread function according to the subject thickness at the pixel position (x,y). The dose Io(x,y) is the dose of radiation which is detected by the radiation detector 5 when it is assumed that there is no subject, and changes depending on the distance (SID) between the X-ray source 3 and a detection surface of the radiation detector 5, the tube voltage, and a mAs value. θx',y' represents a parameter which is specified by the imaging conditions, such as the tube voltage or the characteristic information of the virtual model K.

The estimated image Im may be an image which is estimated to be obtained in a case where radiography of the virtual model K is performed, and may be substantially regarded as an image in which the estimated primary radiation image Igp and the estimated scattered radiation image Igs are synthesized. For example, as shown in FIG. 14, the estimated image Im may be generated by convolution integral of a kernel, in which a primary radiation component and a scattered radiation component are combined, using Expression (15) described below, in place of Expressions (12) to (14). Here, Kp+s(x,y,Tn−1(x',y'),θx',y') is a kernel representing a point spread function in which a primary radiation component and a scattered radiation component are combined. An arbitrary model function may be used as long as an estimated image in which an estimated primary radiation image and an estimated scattered radiation image are synthesized can be generated from an image obtained by radiography.

Ks(x,y,Tn(x',y'),θx',y') and Kp+s(x,y,Tn−1(x',y'),θx',y') can be obtained experimentally according to the imaging conditions or the like.

In this embodiment, while the kernels Ks(x,y,Tn(x',y'),θx',y') and Kp+s(x,y,Tn-1(x',y'),θx',y') may be calculated based on the imaging conditions at the time of imaging, a table in which various imaging conditions are associated with the kernels Ks(x,y,Tn(x',y'),θx',y') and Kp+s(x,y,Tn-1(x',y'),θx',y') is stored in the storage unit 28, the kernels Ks(x,y,Tn(x',y'),θx',y') and Kp+s(x,y,Tn-1(x',y'),θx',y') are obtained based on the irradiation field information, the subject information, and the imaging conditions at the time of imaging with reference to the table.

$$I_m(x, y) = \sum_{x',y'} K_{p+s}(x, y, T_{n-1}(x', y'), \theta_{x',y'})  \quad (15)$$

Subsequent processing will be described according to the flowchart of FIG. 11. Subsequently, the subject thickness distribution determination unit 44 determines whether or not the difference between the radiation image and the estimated image Im satisfies end conditions (Step ST13). Here, as shown in Expressions (16) and (17), an error value $V_{error}$ described below representing the difference between the radiation image and the estimated image Im is defined, and it is determined whether or not the error value $V_{error}$ is equal to or less than a threshold as the end conditions. As shown in Expression (17), the sum of the squares of each pixel value of a difference image Id obtained by subtracting the estimated image Im from the radiation image is defined as an error function $f_{error}$. Any determination methods which can determine that, as the end conditions, the difference between the radiation image and the estimated image Im is sufficiently reduced at an allowable level can be applied.

$$V_{error} = f_{error}(I_m(x, y), I(x, y))  \quad (16)$$

$$f_{error}(I_m(x, y), I(x, y)) = \sum_{x,y} (I_m(x, y) - I(x, y))^2  \quad (17)$$

The invention is not limited to the above-described example, and the error function $f_{error}$ can be defined by any methods which represent the difference between the radiation image and the estimated image Im. For example, as shown in Expression (18) described below, the sum of the absolute values of each pixel value of the difference image Id obtained by subtracting the estimated image Im from the radiation image may be defined as the error function $f_{error}$.

$$f_{error}(I_m(x, y), I(x, y)) = \sum_{x,y} |I_m(x, y) - I(x, y)|  \quad (18)$$

In a case where the error value $V_{error}$ does not satisfy the end conditions (Step ST13: No), the subject thickness distribution determination unit 44 performs modification processing for modifying the subject thickness distribution Tn-1 (in a case where n=1, the initial subject thickness distribution T0) (Step ST14).

In order to perform the modification processing of the subject thickness distribution Tn-1, an arbitrary method which can acquire a modification value of each position of the subject thickness distribution Tn-1 such that the difference between the radiation image and the estimated image Im is reduced can be applied. In this embodiment, processing is performed for calculating the subject thickness of the partial area, which makes the difference between the estimated image Im and the radiation image small, while varying the subject thickness distribution Tn-1 of the virtual model K for each partial area including one or more pixels of the virtual model K. Then, the subject thickness distribution of the virtual model is modified by the calculated subject thickness of each partial area.

Specifically, in this embodiment, it is assumed that the modification value of the subject thickness of the subject thickness distribution Tn-1 is obtained using the steepest descent method. It is possible to minimize the output value of the error function $f_{error}$ by repeatedly calculating dTn-1(x,y) based on primary partial differential (gradient) of the error function $f_{error}$ while varying only the subject thickness of one specific coordinate in Tn-1(x,y) among the pixels of the virtual model K using Expressions (19) and (20) described below. Then, the subject thickness of one specific coordinate when the output value of the error function $f_{error}$ is minimized is determined as the modification value of the subject thickness of the specific coordinate. For other pixels, similarly, the modification value of the subject thickness is obtained, whereby the subject thickness distribution of each pixel is modified and a modified subject thickness distribution Tn is acquired.

$$T_n(x, y) = T_{n-1}(x, y) - \alpha dT_{n-1}(x, y)  \quad (19)$$
$$= T_{n-1}(x, y) - \alpha \frac{d}{dT_{n-1}(x, y)} f_{error}$$

$$\frac{d}{dT_{n-1}(x, y)} f_{error} =  \quad (20)$$
$$\sum_{x',y'} (I_m(x', y') - I(x', y')) \frac{d}{dT_{n-1}(x, y)} K_{p+s}(x', y', T_{n-1}(x, y), \theta_{x,y})$$

$$\frac{d}{dT_{n-1}(x, y)} K_{p+s}(x', y', T_{n-1}(x, y), \theta_{x,y}) =  \quad (21)$$
$$K_{p+s}(x', y', T_{n-1}(x, y) + dt, \theta_{x,y}) - K_{p+s}(x', y', T_{n-1}(x, y), \theta_{x,y})$$

However, in Expression (19), α is an update coefficient which is a parameter representing the update speed of the subject thickness. As an example of a method of calculating the differential value portion of Kp+s shown in Expression (20), for example, change in a value when a very small value dt is added to Tn-1(x,y) can be calculated by Expression (21) and can be used as the value of Kp+s of Expression (20). In Expressions (11) to (21), the same elements represented by the same reference numerals, and description thereof will not be repeated. Any optimization methods which minimize the error value $V_{error}$ representing the difference between the radiation image and the estimated image Im can be applied, and for example, a simplex method, the steepest descent method, or a conjugate gradient method can be used.

If the modified subject thickness distribution Tn is acquired, the subject thickness distribution determination unit 44 increases the value of n by 1 to update the value of n (n=n+1), and the virtual model acquisition unit 41 acquires the modified subject thickness distribution Tn (Step ST11). Then, the estimated image generation unit 42 and the subject thickness distribution determination unit 44 respectively execute the processing of Steps ST11 to ST13 on the acquired subject thickness distribution Tn in the same manner as described above. Then, similarly, the modification processing of the subject thickness distribution Tn (Step ST14), the acquisition processing of the virtual model K having the modified subject thickness distribution Tn (Step ST11), the generation processing of a new estimated image Im using the subject thickness distribution Tn (Step ST12), and the processing for determining whether or not the difference between the newly generated estimated image Im and the radiation image satisfies the end conditions (Step ST13) are repeated until the error value $V_{error}$ representing the difference between the radiation image and the estimated image Im satisfies the end conditions.

In a case where it is determined that the error value $V_{error}$ satisfies the end conditions (Step ST13: Yes), the subject thickness distribution determination unit 44 determines the subject thickness distribution Tn used for the error value $V_{error}$ when the end conditions are satisfied as the subject thickness distribution Tk of the radiation image and ends the subject thickness estimation processing (Step ST15).

In the second embodiment, the processing which is performed in the imaging condition acquisition unit 22, the characteristic acquisition unit 23, the distance information acquisition unit 24, the scattered radiation information acquisition unit 25, the correction unit 26, and the scattered radiation elimination unit 27 are the same as those in the above-described first embodiment, and thus, detailed description thereof will not be repeated.

In this way, in the second embodiment, since it is possible to more appropriately eliminate the scattered radiation component according to the estimated subject thickness distribution, it is possible to acquire a radiation image with higher image quality while taking an air gap into consideration.

In the first and second embodiments described above, it is preferable that the scattered radiation elimination processing is performed in a linear space with respect to a radiation dose where the radiation image has a pixel value proportional to the incidence dose to the radiation detector, and then, logarithmic conversion is performed to convert the space to a logarithmic-linear space proportional to a humans' visual sense.

In the first and second embodiments described above, although the characteristic acquisition unit 23 acquires, as the virtual grid characteristic, the scattered radiation transmittance Ts and the primary radiation transmittance Tp, only one of the scattered radiation transmittance Ts and the primary radiation transmittance Tp may be acquired.

In the first and second embodiments described above, although the scattered radiation elimination processing taking an air gap into consideration is performed on the radiation image acquired through imaging without using a grid, a radiation image acquired through imaging using a grid may be processed. In this case, processing for eliminating a stripe pattern due to a grid is performed on the radiation image, and then, the scattered radiation elimination processing is performed. In such scattered radiation elimination processing, a stripe pattern due to a grid may be eliminated from a radiation image captured using a first grid as a desired grid to acquire a radiation image (first grid-use radiation image) with a stripe pattern eliminated, a virtual grid characteristic corresponding to a desired virtual grid may be acquired, and the first grid-use radiation image may be converted such that a scattered radiation component and a primary radiation component in the acquired first grid-use radiation image become a scattered radiation component and a primary radiation component in a radiation image acquired through imaging using a grid (a grid having the scattered radiation transmittance and the primary radiation transmittance of the acquired virtual grid characteristic) corresponding to the acquired virtual grid characteristic. Both of the first grid and the grid corresponding to the virtual grid characteristic may have a high scattered radiation elimination effect, or arbitrary selection may be made according to the purpose or situation. As the processing for eliminating a stripe pattern due to a grid, for example, a method described in JP2012-203504A can be used.

A processed radiation image obtained by applying one virtual grid characteristic (first virtual grid characteristic) to a radiation image captured with no grid and subjecting the radiation image to the scattered radiation elimination processing may be subjected to the scattered radiation elimination processing taking an air gap into consideration in this embodiment. In this case, the first virtual grid characteristic and a first processed radiation image as a processed radiation image applied with the first virtual grid characteristic are acquired, and a second virtual grid characteristic corresponding to a desired virtual grid different from the first virtual grid characteristic is acquired. Then, the first processed radiation image may be converted based on the second virtual grid characteristic such that a scattered radiation component and a primary radiation component in the first processed radiation image become a scattered radiation component and a primary radiation component corresponding to the second virtual grid characteristic. Both of the first virtual grid characteristic and the second virtual grid characteristic may have a high scattered radiation elimination effect, or arbitrary selection may be made according to the purpose or situation.

Such processing is performed, whereby, for example, based on a radiation image (or the first processed radiation image obtained by subjecting the radiation image captured with no grid to the scattered radiation elimination processing based on the first virtual grid characteristic) captured using a grid having a grid ratio of 3:1, it is possible to virtually acquire a processed radiation image as if imaging is performed using a grid having a grid ratio of 10:1 different from the used grid. Conversely, based on a radiation image (or the first processed radiation image obtained by subjecting the radiation image captured with no grid to the scattered radiation elimination processing based on the first virtual grid characteristic) captured using a grid having a grid ratio of 10:1, it is possible to virtually acquire a processed radiation image as if imaging is performed using a grid having a grid ratio of 3:1 different from the used grid. In these cases, even if imaging of the subject is not repeated, since it is possible to easily acquire a radiation image with a converted grid ratio, it is possible to obtain a processed radiation image subjected to the scattered radiation elimination processing using a grid having a desired grid ratio from the radiation image captured with an unintended grid ratio or the above-described first processed radiation image. For this reason, it is possible to meet a demand for observing processed radiation image subjected to the scattered radiation elimination processing with different degrees without reimaging the subject.

As a specific method, for example, in the first embodiment, a table in which each combination of pre-conversion grid information corresponding to a grid before conversion and post-conversion grid information corresponding to a grid after conversion is associated with Sσ representing the characteristics of scattering in Expression (2) is stored in the storage unit 28. In the table, it is assumed that Sσ is obtained in advance by an experiment or the like such that the characteristics of scattering by the grid before conversion can be relatively converted to the characteristics of scattering by the grid after conversion. Then, the scattered radiation information acquisition unit 25 acquires first grid information corresponding to an actually used grid (or a virtual grid)

as the pre-conversion grid information, acquires second grid information corresponding to a desired virtual grid as the post-conversion grid information, and acquires Sσ corresponding to the first grid information and the second grid information based on the above-described table. Then, using Expressions (1) and (2), Io(x,y) is set to, for example, 1, and the primary radiation component Ip(x,y) and the scattered radiation component Is(x,y) are calculated using the acquired Sσ. Then, the scattered radiation content distribution S(x,y) may be calculated based on the calculated primary radiation component Ip(x,y) and scattered radiation component Is(x,y) by Expression (3), and the corrected scattered radiation content distribution Sh(x,y) may be calculated by Expression (4).

The scattered radiation elimination unit 27 acquires a first grid characteristic (primary radiation transmittance Tp1 and scattered radiation transmittance Ts1) corresponding to the actually used grid (or the virtual grid) and a second grid characteristic (primary radiation transmittance Tp2 and scattered radiation transmittance Ts2) corresponding to the desired virtual grid with respect to the scattered radiation transmittance Ts and the primary radiation transmittance Tp of each frequency band shown in Expression (7), and in order to relatively convert the characteristics of scattering by the first grid before conversion to the characteristics of scattering by the second grid after conversion, acquires Tp2/Tp1 as the primary radiation transmittance Tp in Expression (7) and acquires Ts2/Ts1 as the scattered radiation transmittance Ts in Expression (7). Then, the scattered radiation elimination unit 27 may apply the acquired scattered radiation transmittance Ts (=Ts2/Ts1) and the primary radiation transmittance Tp (=Tp2/Tp1) to Expression (5) to obtain the conversion coefficient R, and as in the first embodiment, may perform the scattered radiation elimination processing using the conversion coefficient R. In Expression (5) described above, there is a case where the conversion coefficient R(x,y) has a value greater than 1 in a case where the scattered radiation transmittance Ts2 of the second grid characteristic is greater than the scattered radiation transmittance Ts1 of the first grid characteristic.

The first grid characteristic and the second grid characteristic may be acquired by an arbitrary method. For example, a table in which a grid characteristic (primary radiation transmittance Tp and scattered radiation transmittance Ts) obtained in advance by an experiment or the like is associated with each piece of grid information is prepared and stored in the storage unit 28. Then, the scattered radiation elimination unit 27 may acquire first and second grid information, and may acquire the first grid characteristic and the second grid characteristic corresponding to the first and second grid information based on the table. The first and second grid characteristics may be acquired based on a user's input from the input unit 7. The grid information may be acquired by an input from the input unit 7, or for example, as described in JP2003-260053A, grid information may be acquired by forming a protrusion according to the type of a grid in a grid and detecting the protrusion.

There is a case where imaging is performed without using a scattered radiation elimination grid depending on an imaging region. It is not preferable that the scattered radiation elimination processing of the first and second embodiments described above is performed on a radiation image acquired by imaging such a region. For this reason, it is preferable to switch on/off the scattered radiation elimination processing of this embodiment according to an imaging region. Information of an imaging region may be acquired by an operator's input or may be automatically acquired from an imaging request input to a known console PC (not shown) which controls an imaging flow, or information which is stored in a system incidental to a radiation image after imaging may be used. In a case where such information cannot be acquired, region recognition processing may be performed on the radiation image to acquire information of an imaging region. In this case, a table in which processing on/off is associated with a region may be stored in the storage unit 28, and processing on/off may be switched with reference to the table.

In the first and second embodiments described above, both of the processed radiation image and the radiation image before processing may be displayed, and any radiation image which is used for diagnosis may be selected.

There is a case in which time-dependent comparison and observation is performed, using the previous radiation images, in order to diagnose the state of healing or the state of progress of a disease. In a case where a radiation image (referred to as a first radiation image) which is captured without using a scattered radiation elimination grid is compared with a radiation image (referred to as a second radiation image) which is captured using the scattered radiation elimination grid, it is preferable to modify the conditions of the scattered radiation elimination processing of this embodiment based on the processing conditions when processing for eliminating a stripe pattern due to a grid is performed for the first radiation image such that the first and second radiation images have the same image quality.

In the above-described embodiments, although the scattered radiation elimination processing is performed using the radiation image acquired in the imaging device 1 which captures the radiation image of the subject using the radiation detector 5, the invention can be of course applied even in a case where radiation image information of a subject is stored and recorded in a storage phosphor sheet as a radiation detecting body shown in JP1996-266529A (JP-H08-266529A), JP1997-024039A (JP-H09-024039A), or the like, and a radiation image acquired by photoelectrically reading the radiation image information from the storage phosphor sheet.

In the first and second embodiments described above, although the scattered radiation elimination processing using the virtual grid characteristic described in JP2014-207958A has been described, for example, as described in U.S. Pat. No. 8,064,676B, the invention can be of course applied even to a method which performs the scattered radiation elimination processing by multiplying a low frequency component by a gain according to the layer of the low frequency component of a radiation image and the pixel value of the low frequency component without using a virtual grid characteristic.

Hereinafter, the functional effects of this embodiment will be described.

The scattered radiation component information is acquired also based on the imaging conditions, whereby it is possible to perform the scattered radiation elimination processing with higher accuracy.

The distance between the subject and the radiation detector is measured to acquire the distance information, whereby it is possible to perform the scattered radiation elimination processing according to an actual distance of an air gap with higher accuracy.

The distance information is acquired according to the imaging region and the imaging direction of the subject, whereby it is possible to make the configuration of the device simple and inexpensive since means for measuring the distance is not required.

What is claimed is:

1. A radiation image processing device which performs processing for eliminating scattered radiation included in radiation transmitted through a subject on a radiation image acquired by detecting radiation transmitted through the subject with a radiation detector, the radiation image processing device comprising:
    a memory in which a plurality of commands are stored; and
    a processor configured to execute the plurality of commands stored in the memory;
    the processor executing processes of:
    acquiring imaging conditions at a time of an acquisition of the radiation image;
    acquiring distance information representing a distance between the subject and the radiation detector;
    acquiring scattered radiation component information representing a scattered radiation component of radiation included in the radiation image based on at least the imaging condition;
    correcting the scattered radiation component information based on the distance information; and
    performing scattered radiation elimination processing of the radiation image based on the corrected scattered radiation component information.

2. The radiation image processing device according to claim 1,
    wherein the imaging conditions include at least one of the distance between a radiation source which irradiates the subject with the radiation and the radiation detector, a quality of the radiation, or a dose of the radiation.

3. The radiation image processing device according to claim 1,
    wherein the process of correcting the scattered radiation component information acquires a ratio of a scattered radiation dose reaching the radiation detector according to a thickness of the subject and the distance information and corrects the scattered radiation component information based on the ratio.

4. The radiation image processing device according to claim 1,
    wherein the process of acquiring distance information acquires the distance information using a sensor for distance measurement.

5. The radiation image processing device according to claim 1,
    wherein the process of acquiring distance information comprises acquiring the distance information based on an imaging region and an imaging direction of the subject.

6. The radiation image processing device according to claim 5,
    wherein the process of acquiring distance information further comprises acquiring the distance information with reference to a table in which a relationship between various imaging regions, various imaging directions, and the distance information is defined.

7. A radiation image processing method which performs processing for eliminating scattered radiation included in radiation transmitted through a subject on a radiation image acquired by detecting radiation transmitted through the subject with a radiation detector, the radiation image processing method comprising:
    acquiring imaging conditions at a time of an acquisition of the radiation image;
    acquiring distance information representing a distance between the subject and the radiation detector;
    acquiring scattered radiation component information representing a scattered radiation component of radiation included in the radiation image based on at least the imaging condition;
    correcting the scattered radiation component information based on the distance information; and
    performing scattered radiation elimination processing of the radiation image based on the corrected scattered radiation component information.

8. A non-transitory computer-readable recording medium having stored therein a radiation image processing program which causes a computer to execute a radiation image processing method performing processing for eliminating scattered radiation included in radiation transmitted through a subject on a radiation image acquired by detecting radiation transmitted through the subject with a radiation detector, the radiation image processing program causing the computer to execute:
    a procedure for acquiring imaging conditions at a time of an acquisition of the radiation image;
    a procedure for acquiring distance information representing a distance between the subject and the radiation detector;
    a procedure for acquiring scattered radiation component information representing a scattered radiation component of radiation included in the radiation image based on at least the imaging condition;
    a procedure for correcting the scattered radiation component information based on the distance information; and
    a procedure for performing scattered radiation elimination processing of the radiation image based on the corrected scattered radiation component information.

* * * * *